(12) United States Patent
Padmos et al.

(10) Patent No.: US 11,742,061 B2
(45) Date of Patent: Aug. 29, 2023

(54) SYSTEMS AND METHODS FOR MANAGING CLINICAL TRIALS

(71) Applicant: Flatiron Health, Inc., New York, NY (US)

(72) Inventors: Alexander Padmos, New York, NY (US); Angel Leung, Richmond, VA (US); Joshua Buddle, Brooklyn, NY (US); Lauren Sutton, Cary, NC (US); Max Tromanhauser, New York, NY (US); Shannon Lee, New York, NY (US); Anthony Hogan, Louisville, KY (US)

(73) Assignee: Flatiron Health, Inc., New York, NY (US)

( * ) Notice: Subject to any disclaimer, the term of this patent is extended or adjusted under 35 U.S.C. 154(b) by 82 days.

(21) Appl. No.: 17/141,132

(22) Filed: Jan. 4, 2021

(65) Prior Publication Data

US 2022/0215908 A1 Jul. 7, 2022

(51) Int. Cl.
*G06F 3/048* (2013.01)
*G16H 10/20* (2018.01)
*G16H 10/60* (2018.01)
*G06F 16/2455* (2019.01)
*G06F 3/0482* (2013.01)

(52) U.S. Cl.
CPC ........... *G16H 10/20* (2018.01); *G06F 3/0482* (2013.01); *G06F 16/2455* (2019.01); *G16H 10/60* (2018.01)

(58) Field of Classification Search
CPC ........ G16H 10/20; G16H 10/60; G16H 15/00; G16H 40/20; G16H 70/20; G16H 70/40; G06F 3/0482
See application file for complete search history.

(56) References Cited

U.S. PATENT DOCUMENTS

| | | | |
|---|---|---|---|
| 2016/0314280 A1 | 10/2016 | Fusari et al. | |
| 2017/0161436 A1* | 6/2017 | MacClary | G06F 16/27 |
| 2020/0176090 A1* | 6/2020 | Batra | G16H 10/60 |
| 2022/0036978 A1* | 2/2022 | Pooleery | G16H 10/20 |

OTHER PUBLICATIONS

Search Report and Written Opinion issued in PCT International Application No. PCT/US2021/064921, dated Apr. 4, 2022 (15 pages).

\* cited by examiner

*Primary Examiner* — Claudia Dragoescu
(74) *Attorney, Agent, or Firm* — Finnegan, Henderson, Farabow, Garrett & Dunner, L.L.P.

(57) ABSTRACT

Systems and methods may manage one or more clinical trials. In one implementation, a system for creating a query for a trial includes at least one processor programmed to: cause a computing device associated with a sponsor of the trial to display a graphical user interface comprising a plurality of patient identifiers associated with the trial; receive, from the computing device, a selection of one of the plurality of patient identifiers; receive, from the computing device, a query comprising an inquiry relating to the selected patient identifier; and transmit the query to a practice site associated with the selected patient identifier.

19 Claims, 9 Drawing Sheets

300

Practice ABX — 311

Search for patient name or PSN — 312

Create Query — 313

| PSN | Patient Name | Date Created | Date Answered | Query Type | Query Status |
|---|---|---|---|---|---|
| 1234567 | Jane Doe | October 14, 2020 | | Inclusion criteria | Open |
| 1234567 | Jane Doe | October 14, 2020 | | Exclusion criteria | Open |
| 3523425 | Dan Smith | October 10, 2020 | | Consent process | Open |
| 3523425 | Dan Smith | October 10, 2020 | October 10, 2020 | Patient status | Answered |
| 2342222 | John Doe | October 4, 2020 | October 4, 2020 | Patient status | Answered |
| 2342222 | John Doe | October 4, 2020 | October 4, 2020 | Tissue sample | Closed |
| 2342222 | John Doe | October 4, 2020 | | Tissue sample | Cancelled |

Create new query

Study patient*

[Search for patient by name of PSN 🔍]

Recently selected:

| PSN# 123456 | Jane Doe | MRN# 3423352 |
| PSN# 123457 | John Doe | MRN# 3423353 |

Query type*

[Inclusion criteria ▼]

Query content*

[Enter query]

[Cancel]

| Trials | Patients |
|---|---|

Trial ABC
GENERAL
Overview
Trial Info
Documents
  Management
  Regulatory submission
QUERIES
PATIENTS
Pre-consent (3)
Consented, Screening (0)
On Trial, Enrolled (0)
Off Trial (0)

— 501
— 502

Queries from  Jane Doe   PSN# 123456   SITE: 101 (Practice ABC)   Close — 520

Open queries    Open queries: 2   Answered query: 1   Closed queries: 0   Cancelled queries: 0 — 521

PSN  [Search by query number 🔍]  Sort by: Most recent ▼
[123456]

— 522

Query # 2322  [OPEN]
● 12/14/2020  Created by admin1@adminstrator1.com on 12/14/2020
       at 02:34 PM [QUERY CONTENT]
○ 12/18/2020  Provide response    Submit response

— 523
— 524

Query # 1233  [ANSWERED]
● 12/10/2020  Created by admin1@adminstrator1.com on 12/10/2020 at 02:34 PM
       [QUERY CONTENT]
● 12/12/2020  Answered by user1234@practiceabc.com on 12/12/2020 at 01:12 PM
       [RESPONSE CONTENT]
○ 12/18/2020  Add note...

| 802 | CAUSE A COMPUTING DEVICE ASSOCIATED WITH A PRACTICE SITE TO DISPLAY A USER INTERFACE CONFIGURED TO DISPLAY A QUERY FOR A TRIAL CONDUCTED AT THE PRACTICE SITE |

↓

| 804 | RECEIVE, FROM THE COMPUTING DEVICE, INFORMATION RESPONSIVE TO THE INQUIRY INCLUDED IN THE QUERY |

↓

| 806 | UPDATE, BASED ON THE RECEIVED INFORMATION, A DATABASE STORING THE TRIAL DATA |

*FIG. 8*

SYSTEMS AND METHODS FOR MANAGING CLINICAL TRIALS

BACKGROUND

Technical Field

The present disclosure relates to managing information related to one or more patients and one or more clinical trials.

Background Information

Managing data for clinical trials has become increasingly challenging. A clinical trial (e.g., a program aimed at developing and/or evaluating a new drug) is usually conducted at various practice sites (e.g., physician's offices, hospitals, academics, etc.) and patients at each practice site can be participants in the trial. Trial data may be received from these practice sites over the Internet or other types of networks in an incremental fashion. Compiling and managing the trial data collected by different practice sites is even more challenging when information for certain patient participants in the trial needs to be updated or verified. For example, a sponsor of a clinical trial may have questions or need additional information relating to data collected for certain patients participating in the clinical trial. However, each of the patients may be associated with a different practice site. With existing data management systems, the sponsor may have to send questions to practice sites on an individual basis through, for example, an email system or other system that is specific to a particular trial. Contacting the different practice sites individually for each particular trial and tracking responses is not only tedious and time-consuming but also prone to introducing errors in the data.

Further, existing data management systems that are often run by third parties (i.e., by a party other than the sponsor or the practice site) are not suitable for managing data for trials that are associated with a variety of different trial sponsors that, in turn, interact with numerous practice sites. As a result, the challenges that were discussed above are multiplied for an entity that provides data management solutions to multiple trial sponsors. For example, an entity managing trial data for multiple trial sponsors will typically need to provide functionality for the trial sponsors to request clarification of patient data or request additional patient data from the practice sites, and provide functionality for the trial sponsors to review responses to these inquiries from the practice sites. With existing management systems, an entity managing trial data for different trial sponsors is faced with designing and regularly updating its system so that it is capable of communicating and interacting with numerous systems across the trial sponsors and practice sites.

In addition, a sponsor of a clinical trial may employ a manager to oversee the collection of its trial data. Clinical trial managers may have responsibility for the management of multiple clinical trials on behalf of a single sponsor, or a particular trial manager may manage multiple trials on behalf of multiple sponsors. Using current tools, a manager will typically need to engage in a time-consuming and inefficient process that involves logging into numerous separate systems to access trial data for each trial the manager oversees.

Therefore, it is desirable to develop systems and methods for effectively and efficiently managing clinical data for trials using a centralized system.

SUMMARY

Embodiments consistent with the present disclosure include systems and methods for managing information related to a patient and one or more clinical trials.

In one embodiment, a system for creating a query for a trial may include at least one processor programmed to: cause a computing device associated with a sponsor of the trial to display a graphical user interface including a plurality of patient identifiers associated with the trial; receive, from the computing device, a selection of one of the plurality of patient identifiers; receive, from the computing device, a query including an inquiry relating to the selected patient identifier; and transmit the query to a practice site associated with the selected patient identifier. In some embodiments, the at least one processor may be programmed to: receive, from the practice site, a response to the query; and cause at least a portion of the received response to be displayed by the computing device associated with the sponsor. In some embodiments, the selected patient identifier may be associated with a link configured to enable a user associated with the sponsor to access an electronic health record associated with the patient identifier. In some embodiments, the graphical user interface may include a selectable area for creating the query. In some embodiments, the graphical user interface may include a creation date for each of the plurality of queries. In some embodiments, the graphical user interface may include a response date for at least one of the plurality of queries. In some embodiments, the graphical user interface may include a patient identifier for each of the plurality of queries. In some embodiments, the graphical user interface may include a query type and a query status of each of the plurality of queries. In some embodiments, the query type for each of the plurality of queries may include at least one of a trial inclusion criteria type, a trial exclusion criteria type, a consent process type, a patient status type, or tissue sample type. In some embodiments, the query status for each of the plurality of queries may include at least one of an open status, a closed status, an answered status, or a cancelled status.

In one embodiment, a graphical user interface for managing one or more queries associated a trial may include a query information area displaying information identifying a plurality of queries associated with the trial. The information identifying the plurality of queries may include at least a query type and a query status of each of the plurality of queries. The graphical user interface may include a search field configured to enable a user to search for a patient identifier associated with one or more of the plurality of queries, and a selectable area configured to enable the user to create a new query. In some embodiments, the information identifying the plurality of queries may include a creation date for each of the plurality of queries. In some embodiments, the information identifying the plurality of queries may include a response date for at least one of the plurality of queries. In some embodiments, the information identifying the plurality of queries may include a patient identifier for each of the plurality of queries. In some embodiments, each of the patient identifiers may be associated with a link configured to enable the user to access an associated electronic health record. In some embodiments, the query type for each of the plurality of queries may include at least one of a trial inclusion criteria type, a trial exclusion criteria type, a consent process type, a patient status type, or tissue sample type. In some embodiments, the query status for each of the plurality of queries may include at least one of an open status, a closed status, an answered status, or a cancelled status. In some embodiments, the user may be associated with a sponsor of the trial.

In one embodiment, a system for managing trial data may include at least one processor programmed to cause a computing device associated with a practice site to display a user interface configured to display a query for a trial conducted at the practice site. The query may include an inquiry relating to at least one patient included in the trial. The at least one processor may be programmed to receive, from the computing device, information responsive to the inquiry included in the query, and update, based on the received information, a database storing the trial data. In some embodiments, the at least one processor may be programmed to transmit the received information to a computing device associated with a sponsor of the trial. In some embodiments, the at least one processor may be programmed to modify at least one word included in the received information prior to transmitting the received information to the computing device associated with the sponsor of the trial. In some embodiments, the at least one processor may be programmed to redact or remove at least one word included in the received response prior to transmitting the received information to the computing device associated with the sponsor of the trial. In some embodiments, the query may be associated with a patient and the received information may be associated with a link providing access to an electronic health record of the patient. In some embodiments, the query may be associated with a patient and the received information includes at least a portion an electronic health record of the patient. In some embodiments, the inquiry included in the query includes at least one of a request for additional data or corrected data relating to a patient participating in the trial. In some embodiments, the query may be associated with a link configured to enable a user associated with the practice site to access an electronic health record of a patient associated with the query.

In one embodiment, a system for managing queries for patient trials may include at least one processor programmed to: receive a first query, wherein the first query may include an inquiry may be associated with a first patient enrolled in a first trial; receive a second query, wherein the second query may include an inquiry associated with a second patient enrolled in a second trial; determine a first practice site associated with the first patient and a second practice site associated with the second patient; cause a first computing device associated with the first practice site to display a first graphical user interface including the first query; cause a second computing device associated with the second practice site to display a second graphical user interface including the second query; receive, from the first computing device, a response to the first query; and receive, from the second computing device, a response to the second query. In some embodiments, the first query and the second query may be received from a third computing device associated with a sponsor of the first and second trials, and the at least one processor may be programmed to cause the third computing device to display a graphical user interface configured to receive the first and second queries. In some embodiments, the at least one processor may be programmed to cause the third computing device to display the response to the first query and the response to the second query. In some embodiments, the graphical user interface may be configured to display a list of a plurality of trials associated with the sponsor. In some embodiments, the at least one processor may be configured to receive, from the third computing device, a selection of one of the plurality of trials associated with the sponsor. In some embodiments, the at least one processor may be configured to cause the third computing device to display a plurality of patient identifiers associated with selected trial. In some embodiments, the first query may be received from a third computing device associated with a first sponsor of the first trial and the second query may be received from a fourth computing device associated with a second sponsor of the second trial, and the at least one processor may be programmed to: cause the third computing device to display a third graphical user interface configured to receive the first query; and cause the fourth computing to display a fourth graphical user interface configured to receive the second query. In some embodiments, the at least one processor may be programmed to cause the third computing device to display the response to the first query, and the fourth computing device to display the response to the second query. In some embodiments, the third graphical user interface may be configured to display a first list of a plurality of trials associated with the first sponsor, and the fourth graphical user interface may be configured to display a second list of a plurality of trials associated with the second sponsor. In some embodiments, the at least one processor may be configured to: receive, from the third computing device, a selection of one of the plurality of trials associated with the first sponsor; and receive, from the fourth computing device, a selection of one of the plurality of trials associated with the second sponsor. In some embodiments, the at least one processor may be configured to cause the third computing device to display a plurality of patient identifiers associated with selected trial received from the third computing device, and the fourth computing device to display a plurality of patient identifiers associated with selected trial received from the fourth computing device. In some embodiments, the first query or the second query may include at least one of a trial identifier, a patient identifier, or a query type.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 3 is a diagram illustrating an exemplary graphical user interface for viewing queries, consistent with the present disclosure.

FIG. 4 is a diagram illustrating an exemplary graphical user interface for creating a query, consistent with the present disclosure.

FIGS. 5A and 5B are diagrams illustrating an exemplary graphical user interface for viewing queries, consistent with the present disclosure.

FIGS. 6, 7, and 8 are flowcharts illustrating exemplary processes for managing trial data.

DETAILED DESCRIPTION

Figure 1:
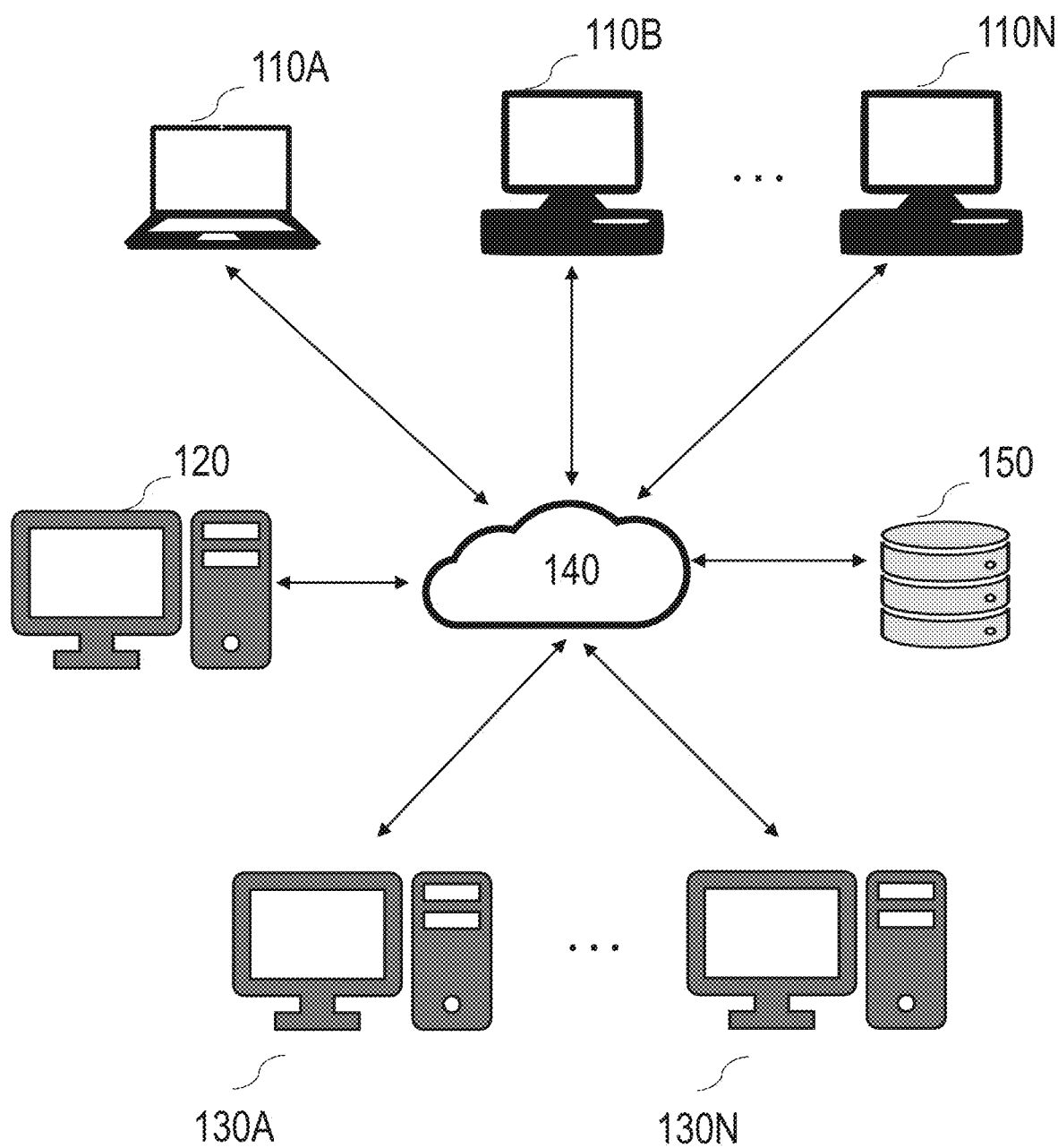
FIG. 1 is a block diagram illustrating an exemplary system for managing data relating to clinical trials, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, non-volatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

As discussed in the background section of this disclosure, managing clinical data is technically challenging for trial sponsors, given that trial data is typically collected at numerous practice sites. This disclosure provides systems and methods for efficiently managing large volumes of clinical data for one or more trials (e.g., trials for newly developed drugs) supervised by a sponsor or different sponsors. For example, the disclosed systems and methods may provide a central location for managing trial data that may be received from computing devices at a multitude of practice sites. The disclosed systems and methods may provide tools for timely communicating queries relating to trials to practice sites and updating trial data based on new data and/or updated information received from the practice sites. Additionally, the disclosed systems and methods may provide tools that allow practice sites to respond to a query relating to one or more trials, by, for example, providing an interactive graphical user interface for displaying information relating to the query and providing data relating to the trial such that a user (e.g., a physician or office staff) may create a response to the query more efficiently. Moreover, the disclosed systems and methods may provide tools for automatically generating audit records documenting trial data records along with one or more queries and query responses (if any).

As an example, in an embodiment, a system may manage trial data for multiple clinical trials and receive queries from one or more sponsors (or from a trial manager). The system may then automatically transmit a query received from a sponsor (or a manager) to an appropriate practice site. At the practice site, the system may cause the query to be displayed to a person (e.g., a physician or office staff) at the practice site and display documents to which the query relates. After the person at the practice site enters a response to the query, the system may automatically update the database and store a record of the resolved query. The sponsor (or trial manager) may then review the response and any documents related to the response.

FIG. 1 illustrates an exemplary system 100 for implementing embodiments consistent with the present disclosure, described in detail below. As shown in FIG. 1, system 100 may include one or more clinical devices 110, a data management device 120, one or more sponsor devices 130, a network 140, and a database 150. It will be appreciated from this disclosure that the number and arrangement of these components are exemplary and provided for purposes of illustration. Other arrangements and numbers of components may be used without departing from the teachings and embodiments of the present disclosure.

A clinical device 110 (e.g., clinical device 110A, 110B, . . . , 110N) may be configured to collect data relating to one or more clinical trials. In some embodiments, a clinical device 110 may be associated with a clinical practice site. A clinical practice site (also referred to herein as a practice site) is a location where a clinical trial is conducted with one or more patients. A practice site may include a physician's office, a clinic, a hospital, a research institute, a higher education institute, or the like. For example, a physician may cooperate with a sponsor of a clinical trial and conduct a trial study on one or more consented human subjects (e.g., one or more patients) for observational trials (i.e., trials that involve certain) interventions but no experimental drugs) and interventional trials (i.e., trials that involve an experimental drug. The physician may collect data relating to the patient before and after the patient has been administered the drug, or a specific intervention, including, for example, measurements of various health parameters. Collected data may include unstructured data and/or structured data. Unstructured data may include information about the patient that is not quantifiable or easily classified, such as such as a physician's description of a treatment plan, notes describing what happened at a visit, statements or accounts from a patient, subjective evaluations or descriptions of a patient's well-being, radiology reports, pathology reports, etc. Structured data may include quantifiable or classifiable data about the patient, such as gender, age, race, weight, vital signs, lab results, date of diagnosis, diagnosis type, disease staging (e.g., billing codes), therapy timing, procedures performed, visit date, practice type, insurance carrier and start date, medication orders, medication administrations, or any other measurable data about the patient.

Data management device 120 may be configured to receive the data relating to a clinical trial and/or a patient participating in the clinical trial from a clinical device 110. For example, data management device 120 may receive information relating to a patient participating in the trial, information relating to the trial, and/or information relating to the practice site.

Data management device 120 may also provide a graphical user interface to a clinical device 110 for displaying the query. Clinical device 110 may receive input from a user of clinical device 110 in response to the query via the graphical user interface provided by data management device 120. Clinical device 110 may also transmit the information responsive to the query to data management device 120. Data management device 120 may update the trial data associated with the query based on the received information.

Information associated with a query may include at least one of a name of a trial, an identity of a trial, a query type, a query status, a creation date, one or more practice sites conducting the trial, a patient's name, a patient identifier, a response date of the query, or the like, or a combination thereof. The query type of a particular query may include a trial inclusion criteria type, a trial exclusion criteria type, a patient condition type, a request for additional patient information type, or the like, or a combination thereof. The query status of a particular query may include at least one of an open status, a closed status, an answered status, a canceled status, or the like, or a combination thereof. In some embodiments, the information relating to the query may include information relating to one or more electronic health records associated with the query. For example, a link providing access to one or more electronic health records associated with the query may be displayed in the graphical user interface provided to a user. Alternatively or additionally, data management device 120 may obtain information relating to one or more electronic health records associated with the query, and the graphical user interface provided to a user may include the obtained information.

Data management device 120 may transmit the data relating to a clinical trial to a sponsor of the clinical trial via network 140 to, for example, sponsor device 130 (e.g., sponsor device 130A, . . . , sponsor device 130B). A sponsor of a trial refers to an owner or a party that is responsible for overseeing the trial, including various tasks such as designing the trial study, facilitating funding, and developing trial protocols. A sponsor may be an individual or an entity, such as pharmaceutical company, or an entity collecting trial data on behalf of a third party. In some embodiments, data management device 120 may provide a graphical user interface to a sponsor device 130 (and/or clinical device 110) for displaying information relating to a trial. For example, data management device 120 may cause sponsor device 130 associated with a sponsor of a trial to display a graphical user interface similar to graphical user interface 300 illustrated in FIG. 3 (and/or graphical user interface 500 illustrated in FIGS. 5A and 5B), which may include a plurality of patient identifiers (e.g., the names of the patients) associated with the trial. The graphical user interface may also include other information identifying one or more queries as described elsewhere in this disclosure.

In some embodiments, the graphical user interface provided to a user of data management device 120 and/or a user of sponsor device 130 may include an input field for creating a new query. For example, the graphical user interface may include a button that, when it is clicked or selected by a user, may cause the graphical user interface to display an area for receiving information relating to the new query. By way of example, FIG. 4 illustrates an exemplary graphical user interface 400 for creating a new query. As illustrated in FIG. 4, via graphical user interface 400, the user may enter information, such as the name of the trial associated with the new query, an identity of the trial, the practice site(s) to send the query, the type of query, the content of the query, etc. Data management device 120 (and/or sponsor device 130) may create the new query based on the information received from the user. For example, data management device 120 may receive from sponsor device 130 a query including an inquiry relating to the patient name selected by the user of sponsor device 130 via graphical user interface 300.

In some embodiments, data management device 120 may transmit a query associated with a trial to a practice site. For example, data management device 120 may provide, to a clinical device 110 associated with a practice site, a user interface configured to display information relating to one or more queries associated with one or more trials conducted at the practice site. For example, data management device 120 may cause clinical device 110 to display a graphical user interface to display information identifying one or more queries associated with one or more trials. By way of example, clinical device 110 may display a graphical user interface similar to graphical user interface 300 illustrated in FIG. 3 (and/or graphical user interface 500 illustrated in FIGS. 5A and 5B). The graphical user interface may also include other information identifying one or more queries as described elsewhere in this disclosure.

Data management device 120 may also receive, from clinical device 110, information responsive to a query. For example, a user of clinical device 110 may input information for responding to an inquiry included in a query associated with a trial (e.g., an inquiry for additional information relating to a patient) via an input device of clinical device 110. Clinical device 110 may transmit the information responsive to the inquiry to data management device 120. In some embodiments, data management device 120 may update the status of the query based on the received information. Alternatively or additionally, data management device 120 may update the trial data relating to the query based on the received information.

In some embodiments, data management device 120 may transmit the information responsive to a query received from clinical device 110 to sponsor device 130. For example, data management device 120 may cause sponsor device 130 to display a graphical user interface for displaying the requested information relating to a patient specified in a query.

In some embodiments, data management device 120 may manage queries for a plurality of trials. For example, data management device 120 may receive a first query, which may include an inquiry associated with a first patient enrolled in a first trial. Data management device 120 may also receive a second query, which may include an inquiry associated with a second patient enrolled in a second trial. Data management device 120 may further determine a first practice site associated with the first patient and a second practice site associated with the second patient. Data management device 120 may also cause a first clinical device 110A associated with the first practice site to display a first graphical user interface including the first query. Data management device 120 may further cause a second clinical device 110B associated with the second practice site to display a second graphical user interface including the second query. Data management device 120 may also receive, from first clinical device 110A, a response to the first query. Data management device 120 may further receive, from second clinical device 110B, a response to the second query.

In some embodiments, alternative to or addition to sending a query to clinical device 110, data management device 120 may generate a response to the query based on the existing trial data. The query may include an inquiry requesting information relating to the conditions of a patient who has been administered an experimental drug. Data management device 120 may obtain the existing trial data relating to the patient (e.g., an electronic health record of the patient) from a database (e.g., database 260 illustrated in FIG. 2 and described below) and locate the requested information. Data management device 120 may also generate a response with the requested information and transmit the response to sponsor device 130. Alternatively, data management device 120 may compile the requested information (or at least a portion thereof) based on the existing trial data and transmit the information to clinical device 110 along with the query. For example, data management device 120 may cause clinical device 110 to display the query in a graphical user interface, and a user of clinical device 110 may click the query in the graphical user interface, which may display detailed information of the query. The graphical user interface may also display the information compiled by data management device 120.

In some embodiments, data management device 120 may create an audit record associated with a trial, which may include trial data received from clinical devices 110, one or more queries sent to (or provided to) clinical devices 110, and one or more responses to one or more queries received from clinical devices 110. Data management device 120 may also transmit the audit record to sponsor device 130.

Network 140 may be configured to facilitate communications among the components of system 100. Network 140 may include a local area network (LAN), a wide area network (WAN), portions of the Internet, an Intranet, a cellular network, a short-ranged network (e.g., a Bluetooth based network), or the like, or a combination thereof.

Database 150 may be configured to store information and data for one or more components of system 100. For example, database 150 may store electronic health records associated with one or more patients. Database 150 may also store information relating to one or more trials. For example, database 150 may store data relating to a patient participating a clinical trial. In some embodiments, database 150 may also store one or more algorithms for creating a query (or a portion thereof) based on the data from a clinical device 110. Clinical devices 110, data management device 120, and/or sponsor devices 130 may be configured to access and obtain the data stored on database 150 via network 140.

Figure 2:
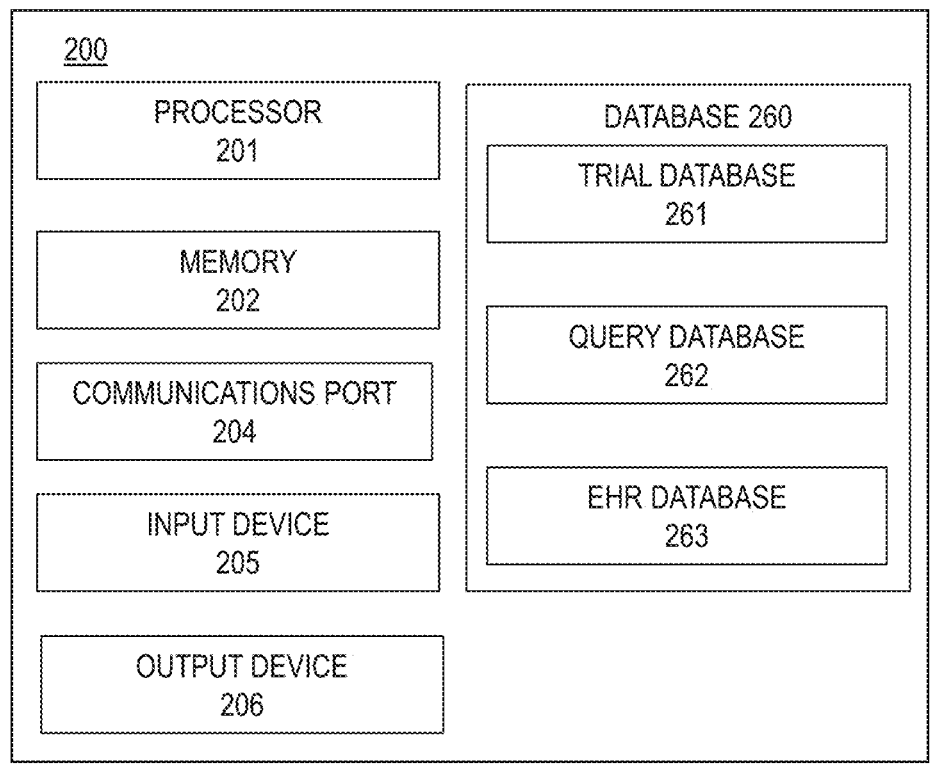
FIG. 2 is a block diagram illustrating an exemplary computing device for managing data relating to clinical trials, consistent with the present disclosure.

FIG. 2 is a block diagram illustrating an exemplary computing device 200. Clinical device 110, data management device 120, and/or sponsor device 130 may be implemented based on the architecture of computing device 200. For example, clinical device 110, data management device 120, and/or sponsor device 130 may include one or more components of computing device 200.

As illustrated in FIG. 2, computing device 200 may include at least one processor (e.g., processor 201), a memory 202, an input device 205, an output device 206, and a database 260.

Processor 201 may be configured to perform one or more functions of the components of system 100 described in this application. Computing device 200 may also include a memory 202 that may store instructions for various components of computing device 200. For example, memory 202 may store instructions that, when executed by processor 201, may be configured to cause processor 201 to perform one or more functions described herein.

Communications port 204 may be configured to receive data from and transmit data to one or more components of computing device 200.

Input device 205 may be configured to receive input from the user of computing device 200, and computing device 200 may perform one or more functions in response to the input received. In some embodiments, input device 205 may include an interface displayed on a touchscreen (e.g., output device 206). Output device 206 may be configured to output information and/or data to the user. For example, output device 206 may include a display configured to display one or more queries created for one or more clinical trials. In some embodiments, output device 206 may include a touchscreen.

Database 260 may be configured to store various data and information for one or more components of computing device 200. For example, in some embodiments, database 260 may include a trial database 261, a query database 262, and an electronic health record (EHR) database 263. Trial database 261 may be configured to store information relating to one or more trials. For example, trial database 261 may store a trial portfolio for each of the trials, which may include data relating to a trial conducted at a plurality of practice sites. In some embodiments, a trial portfolio may also include trial name, trial description, or the like, or a combination thereof. Computing device 200 may obtain information relating to the trials from trial database 261 and modify the information if needed.

Query database 262 may store information relating to one or more queries. A query may include one or more of a name of a patient, an identity associated with a patient, a name of a clinical trial, an identity associated with a clinical trial, a date of creating the query, a type of the query, a status of the query, instructions for the practice site to collect more data relating to a clinical trial, instructions for the practice site to collect more data relating to the patient, or the like, or a combination thereof. In some embodiments, the status of a query comprises at least one of an open status, a closed status, an answered status, or a canceled status.

EHR database 263 may store electronic health records associated with patients. Processor 201 may receive one or more electronic health records from EHR database 263.

FIG. 3 is a diagram illustrating an exemplary graphical user interface 300 for displaying queries, consistent with the present disclosure. Graphical user interface 300 may be displayed by data management device 120 and/or sponsor device 130. For example, a user associated with a sponsor device 130 may interact with graphical user interface 300 for viewing one or more queries associated with one or more trials. As another example, the user may also interact with graphical user interface 300 for creating a new query for a trial.

Graphical user interface 300 may include one or more input fields for receiving input from a user. For example, graphical user interface 300 may include a search field configured to enable a user to search for a patient identifier associated with one or more of the plurality of queries. Graphical user interface 300 may include one or more query information areas for displaying information identifying a plurality of queries associated with one or more trials. For example, as illustrated in FIG. 3, graphical user interface 300 may include a search field 311 for the user to enter information relating to a practice site. By way of example, the user may search or select a particular practice site among a plurality of practice site (e.g., the selected "Practice ABX" shown in FIG. 3) or enter an identity associated with a practice site. All of (or a subset of) the queries relating to one or more trials conducted at the practice site may be displayed in a query information area 321 of graphical user interface 300. As another example, graphical user interface 300 may include a box 312 for searching a particular patient. The user may enter an identifier of a patient (e.g., all or part of the patient's name, a patient identifier, etc.).

One or more queries relating to one or more trials in which the patient participates (and/or participated) may be listed in query information area 321 of graphical user interface 300. Query information area 321 may include information identifying a plurality of queries associated with one or more trials. In some embodiments, the information identifying the plurality of queries comprises at least a query type and a query status of each of the plurality of queries.

In some embodiments, graphical user interface 300 may display queries relating to the same clinical trial that are sent (or to be sent) different clinical devices 110 (i.e., devices associated with different practice sites).

Information associated with and/or identifying a query included in a graphical user interface may include information associated with the query as described elsewhere in this disclosure. For example, information displayed in the graphical user interface and identifying a query may include at least one of a name of a trial, an identity of a trial, a query type, a query status, a creation date, a practice site conducting the trial, a patient's name, a patient's identity, a response date of the query, or the like, or a combination thereof.

Graphical user interface 300 may include one or more queries. For example, as illustrated in FIG. 3, graphical user interface 300 may include information identifying one or more queries in query information area 321. A user may click a particular query (or information identifying a particular query) via an input device, and graphical user interface 300 (or a different user interface) may display the details of the query.

In some embodiments, graphical user interface 300 may include a selectable area (e.g., a button 313 illustrated in FIG. 3) for creating a new query. In response to the input received from the user for creating a new query, data management device 120 (and/or sponsor device 130 and/or clinical device 110) may cause the display to display a user interface for the user to create a new query. By way of example, data management device 120 (and/or sponsor device 130 and/or clinical device 110) may cause the display to display graphical user interface 400 illustrated in FIG. 4 for creating a new query. As illustrated in FIG. 4, the user may enter via graphical user interface 400 information relating to a query, including, for example, various fields such as a name of a patient, an identity associated with of a patient, a name of a clinical trial, an identity associated with a clinical trial, a date of creating the query, a type of the query, a status of the query, content of the query, instructions for the practice site to collect more data relating to a clinical trial, instructions for the practice site to collect more data relating to the patient, or the like, or a combination thereof. In some embodiments, graphical user interface 400 may also display one or more patients for which one or more queries are recently selected, viewed, or created. In some embodiments, a user associated with sponsor device 130 (and/or data management device 120) may initiate a query by entering query information in graphical user interface 400. For example, the user may enter query information in graphical user interface 400 to request a clarification relating to an observation note by a physician. Alternatively or additionally, a user associated with clinical device 110 may initiate a query. For example, the user may enter query information in graphical user interface 400 to request a clarification relating to a trial requirement (e.g., relating to a trial inclusion or exclusion criterium).

Referring to FIG. 3, in some embodiments, graphical user interface 300 may be configured to receive user input relating to one or more queries shown in graphical user interface 300 (e.g., a mouse click or other selection of one of the queries or patients). Graphical user interface 300 may also be configured to display additional information relating to the query. For example, graphical user interface 300 may display detailed information of the query (e.g., instructions for the practice site to collect more data relating to the patient) as a pop-up window overlapping with at least a portion of query information area 321. As another example, graphical user interface 300 may display data of one or more electronic health records associated with the query. By way of example, the query may be a request for a clarification relating to a physician's notes regarding a patient's visit after taking an experimental drug. Data management device 120 may obtain an electronic health record of the patient that includes the relevant notes and provide, to clinical device 110, graphical user interface 300 including the electronic health record (or the relevant notes). A user of clinical device 110 may also enter information to respond to the query (e.g., revising the notes), which may be received by data management device 120 (and/or clinical device 110) and generate a response based on the received input. Alternatively or additionally, additional information associated with the query may include a link providing access to one or more electronic health records associated with the query. Alternatively or additionally, graphical user interface 300 may be configured to receive user input relating to one or more patients shown in graphical user interface 300 (e.g., a mouse click or other selection of one of the queries or patients). Graphical user interface 300 may also be configured to display additional information relating to the patient. For example, graphical user interface 300 may display detailed information of the patient (e.g., instructions for the practice site to collect more data relating to the patient) as a pop-up window overlapping with at least a portion of query information area 321. Additional information may include an electronic health record of the patient (or a link providing access to an electronic health record of the patient).

Figure 5A:
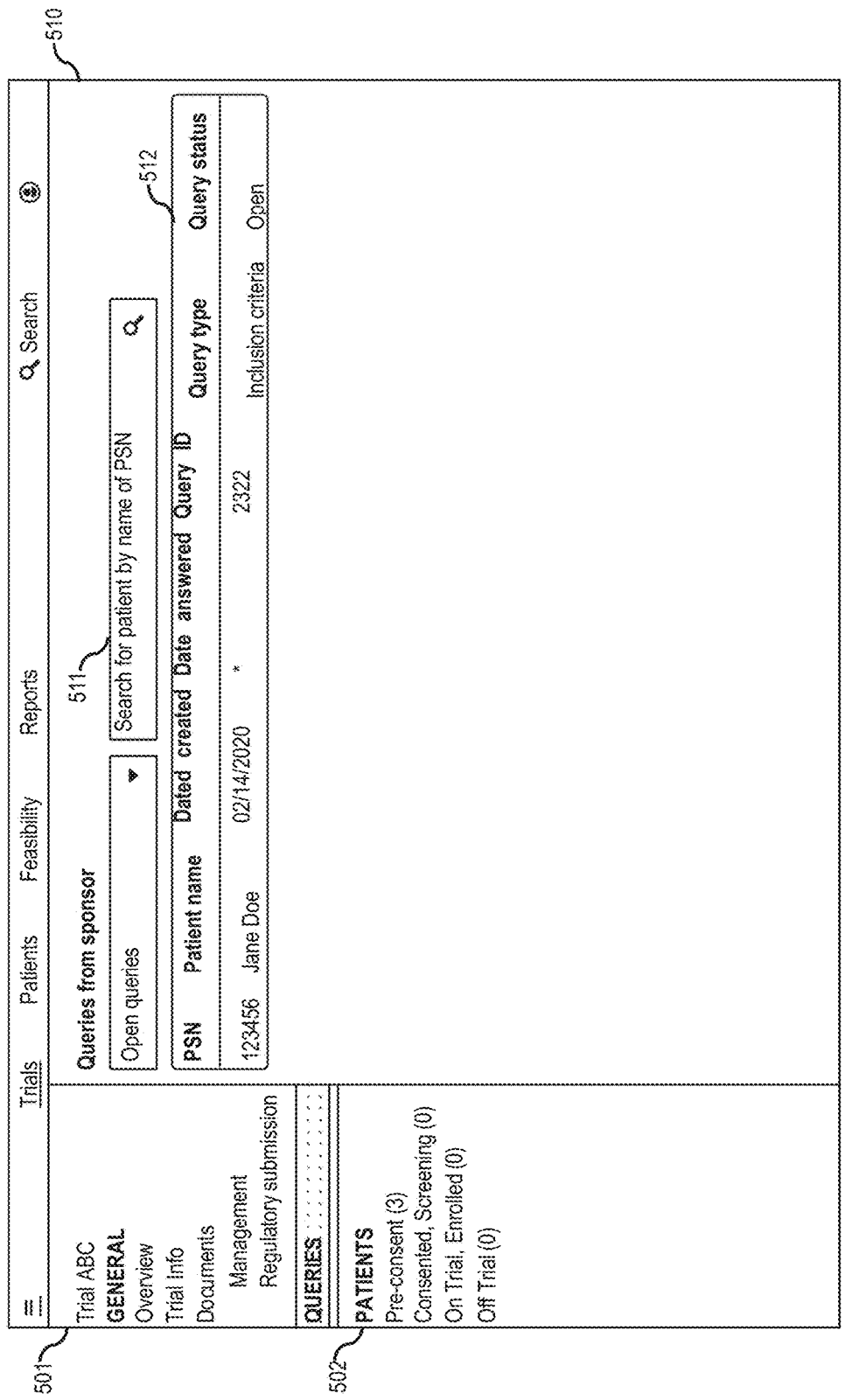

FIGS. 5A and 5B are diagrams illustrating an exemplary graphical user interface 500 for viewing one or more queries. Graphical user interface 500 may be displayed by a display associated with data management device 120, sponsor device 130, and/or clinical device 110 for displaying one or more queries. For example, data management device 120 may cause sponsor device 130 (and/or clinical device 110) to display graphical user interface 500 including one or more queries. As another example, data management device 120 may cause a display associated with data management device 120 to display graphical user interface 500 including one or more queries.

As illustrated in FIG. 5A, graphical user interface 500 may include an area 501 displaying general information relating to a particular trial (e.g., "Trial ABC" illustrated in FIG. 5A). The user may interact with one or more tabs in trial area 501 to view relevant information relating to the trial. In one example, the user may click "Trial Info" tab, and in response to the input, graphical user interface 500 may display the information relating to the trial (e.g., the sponsor of the trial, the status of the trial, and/or other types of information relating to the trial disclosed in this disclosure) in area 510 (or an area overlapping with area 510 or a new window). Graphical user interface 500 may include a filtering area 502 for filter one or more queries that meet a filtering condition. For example, area 502 may include various filters according to a query status, a patient status, a trial status, or the like, or a combination thereof. By way of example, area 502 may include filters for filtering queries based on the patient-trial status. The user may click the "Pre-consent" tab (i.e., a condition in which a patient has a pre-consent status, but he or she has not consented), and graphical user interface 500 may display one or more queries meeting the "Pre-consent" condition in area 510 (or area 512).

Graphical user interface 500 may further include a search field configured to enable the user to search for a patient identifier associated with one or more of the plurality of queries. Graphical user interface 500 may include one or more query information areas for displaying information identifying a plurality of queries associated with one or more trials. For example, as illustrated in FIG. 5A, graphical user interface 500 may include a search field 511 for the user to enter information relating to a patient (e.g., all or part of the patient's name, a patient identifier, etc.). One or more queries relating to one or more trials in which the patient participates (and/or participated) may be listed in query information area 512 of graphical user interface 500. Query information area 512 may include information identifying a plurality of queries associated with one or more trials. In some embodiments, the information identifying the plurality of queries may comprise at least a query type and a query status of each of the plurality of queries and/or other types of information relating to a query disclosed in this disclosure.

In some embodiments, the user may click a patient (e.g., the patient named "Jane Doe") in query information area 512 of graphical user interface 500, and graphical user interface 500 may display additional information relating to the patient and/or one or more queries associated with the patient. For example, graphical user interface 500 may display a query information area 520 illustrated in FIG. 5B, which may overlap with area 510 (only a partial area of which is illustrated in FIG. 5B). As illustrated in FIG. 5B, query information area 521 may include a status area 521 for displaying the numbers of queries based on the query status (e.g., an open status, an answered status, etc.). Query information area 520 may also include one or more query windows for displaying information relating to a query. By way of example, query information area 520 may include a query window 522 for displaying information relating to an open query and a query window 524 for displaying information relating to an answered query. Query window 522 may include information relating to a particular query. For example, query window 522 may include a person (and/or a party) creating the query, the time and/or date of the creation of the query, the status of the query (e.g., open, answered, canceled, closed, etc.), the query content, or the like, or a combination thereof. Query window 522 may also include an area 523 for receiving input from the user relating to a response to the query. For example, the user may type a response to the query in area 523. Alternatively or additionally, the user may attach via graphical user interface 500 one or more documents (or a link to a document) associated with a response to the query. The user may submit a response to the query via graphical user interface 500 (by, for example, click a "Submit response" button in query window 522. In some embodiments, query window 522 may also include a timeline comprising the dates relating to the query. For example, as illustrated in FIG. 5B, query window 522 may include a timeline comprising the creation date "12/14/2020." The timeline may also include a current date ("12/18/2020"). Query window 524 may include information relating to an answered query. For example, query window 524 may include the information relating to the query (dated Dec. 10, 2020) and the information relating to a response to the query (dated Dec. 12, 2020). Query window 524 may also include an area 525 for the user to enter information for sending a follow-up query or a note relating to the query and/or the response. Similar to query window 522, query window 524 may also include a timeline comprising the dates relating to the query, including the creation date and the response date. In some embodiments, the timeline may include a current date ("12/18/2020").

Figure 6:
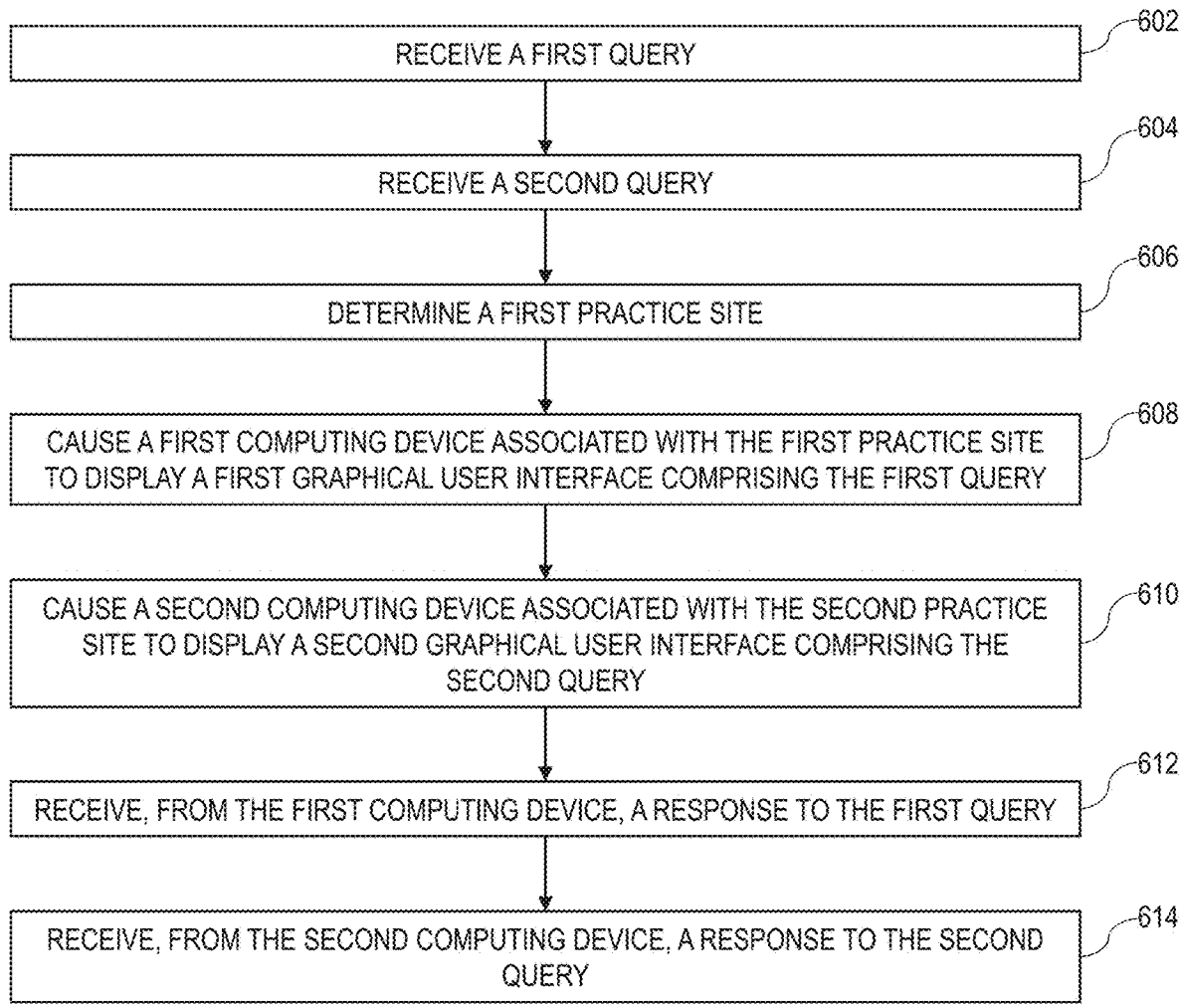

FIG. 6 is a flowchart illustrating an exemplary process 600 for managing trial data, consistent with the present disclosure. While process 600 is described in connection with data management device 120, one skilled in the art would understand that one or more steps of process 600 may be performed by other components of the system (e.g., clinical device 110 and/or sponsor device 130).

At step 602, data management device 120 may receive a first query. The first query may comprise an inquiry associated with a first patient enrolled in a first trial. The term "first patient" used herein refers to a patient enrolled in a trial and does not necessarily mean the patient who is the first person enrolled in the trial. For example, data management device 120 may receive a first query from a first sponsor device 130A associated with a first sponsor.

In some embodiments, the first query may include information associated with the query. For example, the first query may include at least one of a trial identifier (e.g., a trial name, a ClinicalTrials.gov identifier (NCT number)), a query type, a query status, a creation date, a practice site conducting the trial, a patient's name, a patient's identity, a response date of the query, or the like, or a combination thereof.

At step 604, data management device 120 may receive a second query. The second query may include an inquiry associated with a second patient enrolled in a second trial. The term "second patient" used herein refers to a patient enrolled in a trial and does not necessarily mean the patient who is the second person enrolled in the trial. For example, data management device 120 may receive a second query from the first sponsor device 130A associated with the second sponsor. By way of example, data management device 120 may receive from second sponsor device 130B the second query including an inquiry relating to the patient name or patient ID selected by the user of first sponsor device 130A via graphical user interface 300. Alternatively, data management device 120 may receive a second query from a second sponsor device 130B associated with a second sponsor, which is different from the second sponsor.

In some embodiments, data management device 120 may cause a computing device associated with a sponsor to display a graphical user interface (e.g., a graphical user interface similar to graphical user interface 300 illustrated in FIG. 3) configured to receive a query. For example, data management device 120 may cause first sponsor device 130A to display a first graphical user interface (which may be similar to graphical user interface 300 illustrated in FIG. 3) configured to receive the first query. Data management device 120 may also cause second sponsor device 130B to display a second graphical user interface (which may be similar to graphical user interface 300 illustrated in FIG. 3) configured to receive the first query. By way of example, the graphical user interface displayed at a sponsor device 130 (e.g., first sponsor device 130A or second sponsor device 130B) may be configured to display a list of a plurality of trials associated with the sponsor. The graphical user interface may also be configured to receive a selection of one of the plurality of trials from a user of sponsor device 130 (e.g., first sponsor device 130A or second sponsor device 130B). For example, the user may select one of the trials displayed in the graphical user interface via an input device of sponsor device 130 (e.g., first sponsor device 130A or second sponsor device 130B). The graphical user interface may further be configured to display one or more patient identifiers (e.g., patient name or patient ID) associated with the selected trial.

The graphical user interface may also be configured to receive a selection of one (or more) of the one or more patients. The graphical user interface may further be configured to provide the user of sponsor device 130 (e.g., first sponsor device 130A or second sponsor device 130B) an interface for creating a query associated with the selected patient(s). Sponsor device 130 (e.g., first sponsor device 130A or second sponsor device 130B) may transmit the created query to data management device 120. In some embodiments, the graphical user interface may be displayed via a web page or an application page associated with data management device 120. For example, first sponsor device 130A (and/or second sponsor device 130B) may log into a website operated by data management device 120, which may cause first sponsor device 130A (and/or second sponsor device 130B) to display a web page including the graphical user interface for creating and/or viewing one or more queries.

At step 606, data management device 120 may determine a first practice site associated with the first patient and a second practice site associated with the second patient. For example, data management device 120 may determine a practice site associated with the patient based on information associated with the query (the first query and/or the second query) received from a sponsor device 130 (first sponsor device 130A and/or second sponsor device 130B). By way of example, the first query received from first sponsor device 130A may include an identifier of a practice site (e.g., a name or an ID of the practice site) associated with the patient, and data management device 120 may determine the practice site based on the identifier of the practice site by searching a practice site database stored in, for example, database 260. Alternatively or additionally, data management device 120 may determine the first practice site based on a patient identifier and/or a trial identifier associated with the first query. Similarly, data management device 120 may determine a second practice site associated with the second patient based on the information relating to the second query.

At step 608, data management device 120 may cause a first computing device associated with the first practice site to display a first graphical user interface, which may include the first query. For example, data management device 120 may cause a first clinical device 110A associated with the first practice site to display a first graphical user interface including the first query.

In some embodiments, a graphical user interface may be displayed at clinical device 110 via a web page or an application page associated with data management device 120. For example, first clinical device 110A (or other clinical devices 110 described in this disclosure) may log into a website operated by data management device 120, which may cause first clinical device 110A to display a web page including the graphical user interface for viewing one or more queries associated with one or more trials conducted at the practice site. In some embodiments, the graphical user interface may include a plurality of queries associated with one or more trials conducted in the practice site. The graphical user interface may be configured to receive a selection of the queries from a user of first clinical device 110A. In response to the selection, the graphical user interface may also be configured to display more information of the query. For example, the graphical user interface may display a document associated with the query. Alternatively or additionally, the graphical user interface may display a link that may enable first clinical device 110A to access a document and/or an electronic health record associated with the query and/or the patient.

At step 610, data management device 120 may cause a second computing device associated with the second practice site to display a second graphical user interface comprising the second query. For example, data management device 120 may cause second clinical device 110B to display a second graphical user interface including the second query (which may be similar to causing first clinical device 110A to display the first graphical user interface, as described elsewhere in this disclosure).

In some embodiments, the second graphical user interface displayed at second clinical device 110B may be the same as the first graphical user interface displayed at first clinical device 110A. In other embodiments, the second graphical user interface may be different from the first graphical user interface.

At step 612, data management device 120 may receive, from the first computing device, a response to the first query. For example, a first query may request additional information regarding the patient's conditions, and a physician (i.e., a user of first clinical device 110A) may type notes in the graphical user interface displayed at first clinical device 110A in response to the query. The graphical user interface may be configured to receive the typed information and send data management device 120 the received information as a response to the query. In some embodiments, the response to query received from first clinical device 110A may include an electronic health record associated with the patient and/or the first query. Alternatively or additionally, the response may include a link providing access to an electronic health record associated with the patient and/or the first query.

At step 614, data management device 120 may receive, from the second computing device, a response to the second query. For example, a second query may request additional images of the patient's tumor site. A physician (i.e., a user of second clinical device 110B) may obtain the requested images. The graphical user interface displayed at second clinical device 110B may be configured to receive the images and other information typed by the physician (e.g., the descriptions of the images) and send data management device 120 the received images and information as a response to the second query. In some embodiments, the response to query received from second clinical device 110B may include an electronic health record associated with the patient and/or the second query. Alternatively or additionally, the response may include a link providing access to an electronic health record associated with the patient and/or the second query.

In some embodiments, data management device 120 may cause a computing device associated with a sponsor to display a response to a query of a trial associated with the sponsor. For example, the first trial and the second trial may be sponsored by the same sponsor. Data management device 120 may cause a sponsor device 130 associated with the sponsor to display a graphical user interface including the response to the first query (or at least a portion thereof) received from first clinical device 110A. Data management device 120 may also cause sponsor device 130 to display a graphical user interface including the response to the second query (or at least a portion thereof) received from second clinical device 110B. By way of example, sponsor device 130 may log into a website, which may provide a web page including a graphical user interface for viewing one or more queries and/or a response to each of the one or more queries (if any). A user of sponsor device 130 may select a response via the graphical user interface, which, in response, may display detailed information of the response.

In some embodiments, the first trial and the second trial may be associated with different sponsors. For example, the first trial may be associated with the first sponsor, and the second trial may be associated with the second sponsor. As described above, data management device 120 may cause first sponsor device 130A to display a first graphical user interface to receive the first query (associated with the first trial) and cause second sponsor device 130B to display a second graphical user interface to receive the second query (associated with the second trial). Data management device 120 may also be configured to cause first sponsor device 130A to display the response to the first query (or at least a portion thereof) in, for example, the first graphical user interface. Data management device 120 may further be configured to cause second sponsor device 130B to display the response to the second query (or at least a portion thereof) in, for example, the second graphical user interface.

In some embodiments, data management device 120 may modify at least one word included in the received information in response to a query prior to transmitting the received information to sponsor device 130. For example, a physician at a practice site may type "Joe Doe's tissue sample cut from the lesion shows an improvement" in a user interface displayed at clinical device 110. Data management device 120 (and/or clinical device 110) may replace the patient's name "Joe Doe" with a generalized term such as the "PATIENT" and transmit the information with the generalized term to sponsor device 130. Alternatively or additionally, clinical device 110 and/or data management device 120 may redact or remove at least one word included in the received response prior to transmitting the received information to the computing device associated with the sponsor of the trial. For example, data management device 120 may identify in a response personally identifiable information, such as the patient's name, and/or protected health information, such as demographic data, medical histories irrelevant to the trial, test results irrelevant to the trial, insurance information, etc. Data management device 120 may also redact or remove the identified information (e.g., redact the name with a black box) from the response. Data management device 120 may also be configured to transmit to sponsor device 130 the response with the information redacted or removed.

Figure 7:
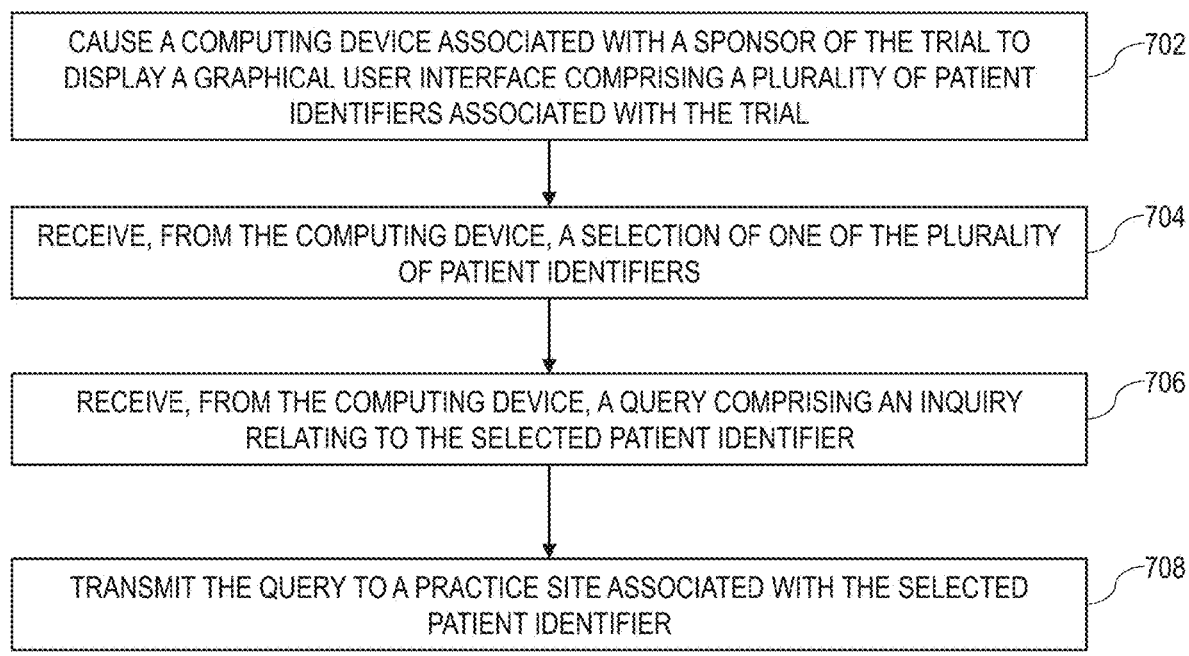

FIG. 7 is a flowchart illustrating an exemplary process 700 for managing trial data, consistent with the present disclosure. While process 700 is described in connection with data management device 120, one skilled in the art would understand that one or more steps of process 700 may be performed by other components of the system (e.g., clinical device 110 and/or sponsor device 130).

At step 702, data management device 120 may cause a computing device associated with a sponsor of the trial to display a graphical user interface comprising a plurality of patient identifiers associated with a trial. For example, data management device 120 may cause sponsor device 130 associated with a sponsor of a trial to display graphical user interface 300 illustrated in FIG. 3, which may include a plurality of patient identifiers (e.g., the names of the patients) associated with the trial. Graphical user interface 300 may also include other information identifying one or more queries as described elsewhere in this disclosure.

At step 704, data management device 120 may receive, from the computing device, a selection of one of the plurality of patient identifiers. For example, data management device 120 may receive from sponsor device 130 a selection by a user of sponsor device 130 of one patient's name via graphical user interface 300.

In some embodiments, the selected patient identifier may be associated with a link configured to enable a user associated with the sponsor to access an electronic health record associated with the patient identifier. For example, the user of sponsor device 130 may select a patient's name or a patient ID display in graphical user interface 300, which may then display a link configured to enable the user to access an electronic health record associated with the patient. Alternatively or additionally, graphical user interface 300 may display information obtained from the electronic health record associated with the patient identifier in, for example, a pop-up window.

As described elsewhere in this disclosure, graphical user interface 300 may also include information identifying one or more queries.

Referring to FIG. 7, at step 706, data management device 120 may receive, from the computing device, a query including an inquiry relating to the selected patient identifier. For example, data management device 120 may receive from sponsor device 130 a query including an inquiry relating to the patient name or patient ID selected by the user of sponsor device 130 via graphical user interface 300.

In some embodiments, the query may be created by a user of sponsor device 130 using graphical user interface 300. For example, as illustrated in FIG. 3, graphical user interface 300 may include a selectable area (e.g., a button 313) for creating a query. The user may interact with graphical user interface 300 to create a new query to be transmitted to data management device 120, as described elsewhere in this disclosure. In some embodiments, an inquiry included in the query may include at least one of a request for additional data or corrected data relating to a patient participating in the trial.

Referring to FIG. 7, at step 708, data management device 120 transmit the query to a practice site associated with the selected patient identifier. For example, data management device 120 may transmit the query to a clinical device 110 associated with the practice site that conducts or conducted the trial with the patient associated with the selected patient identifier. By way of example, data management device 120 may cause clinical device 110 to display a graphical user interface similar to graphical user interface 300 for displaying the query.

In some embodiments, data management device 120 may also receive a response to the query from clinical device 110. For example, a user of clinical device 110 may enter information responsive to the query via graphical user interface 300 (and/or other meanings), and clinical device 110 may generate a response based on the information responsive to the query. Alternatively or additionally, data management device 120 may generate a response based on the information responsive to the query received at clinical device 110. For example, data management device 120 may receive the information responsive to the query received at clinical device 110, and generate a response based on the information responsive to the query.

In some embodiments, data management device 120 may cause at least a portion of the received response to be displayed by the computing device associated with the sponsor. For example, data management device 120 may cause at least a portion of the received response to be displayed by sponsor device 130 associated with the query.

In some embodiments, data management device 120 data management device 120 may also transmit clinical device 110 data related to the information responsive to the query received from clinical device 110. For example, data management device 120 may obtain data from an electronic health record of a patient associated with the query as supplemental information to the information responsive to the query. Data management device 120 may also transmit the information responsive to the query and supplemental information to sponsor device 130. Sponsor device 130 may update the status of the query based on the received information. For example, sponsor device 130 may change the status of the query to a closed status. Alternatively or additionally, sponsor device 130 may create a new query or send an updated query based on the received information. For example, after reviewing the received information, a user of sponsor device 130 may need further information from the practice site. The user of sponsor device 130 may create a new query (or send an updated query) requesting additional information, and transmit the new query (or the updated query) to data management device 120. Data management device 120 may transmit the query to clinical device 110, and clinical device 110 may respond to the query, as described elsewhere in this disclosure.

In some embodiments, data management device 120 may create an audit record associated with a trial, which may include trial data received from clinical devices 110, one or more queries sent to (or provided to) clinical devices 110, and one or more responses to one or more queries received from clinical devices 110. Data management device 120 may also transmit the audit record to sponsor device 130.

FIG. 8 is a flowchart illustrating an exemplary process 800 for managing trial data, consistent with the present disclosure. While process 800 is described in connection with data management device 120, one skilled in the art would understand that one or more steps of process 800 may be performed by other components of the system (e.g., clinical device 110 and/or sponsor device 130).

At step 802, data management device 120 may cause a computing device associated with a practice site to display a user interface configured to display a query for a trial conducted at the practice site. In some embodiments, the query may include an inquiry relating to at least one patient included in the trial. For example, the query may include an inquiry include at least one of a request for additional data or corrected data relating to a patient participating in the trial. In some embodiments, the query may be associated with a link configured to enable a user associated with the practice site to access an electronic health record of a patient associated with the query.

At step 804, data management device 120 may receive, from the computing device, information responsive to the inquiry included in the query. For example, a user of clinical device 110 may enter information responsive to the inquiry (e.g., providing additional information relating to the conditions of the patient associated with the query) via graphical user interface 300. Data management device 120 may receive the information responsive to the inquiry from the clinical device 110.

In some embodiments, clinical device 110 and/or data management device 120 may transmit the received information to a sponsor device 130 associated with a sponsor of the trial. In some embodiments, clinical device 110 and/or data management device 120 may modify at least one word included in the received information prior to transmitting the received information to the computing device associated with the sponsor of the trial. For example, a physician at a practice site may type "Joe Doe's tissue sample cut from the lesion shows an improvement" in a user interface displayed at clinical device 110. Data management device 120 (and/or clinical device 110) may replace the patient's name "Joe Doe" with a generalized term "the PATIENT" and transmit the information with the generalized term to sponsor device 130. Alternatively or additionally, clinical device 110 and/or data management device 120 may redact or remove at least one word included in the received response prior to transmitting the received information to the computing device associated with the sponsor of the trial. For example, data management device 120 may redact the patient's name (e.g., redact the name with a black box) and transmit the information with the redacted name to sponsor device 130.

In some embodiments, the query may be associated with a patient, and the received information responsive to the inquiry may be associated with a link providing access to an electronic health record of the patient. For example, clinical device 110 may transmit a link providing access to an electronic health record of the patient as a part of the information responsive to the inquiry (e.g., an electronic health record including a physician's notes describing the patient's conditions after taking an experimental drug). Alternatively or additionally, the received information responsive to the inquiry may include at least a portion of an electronic health record of the patient.

At step 806, data management device 120 may update, based on the received information, a database storing the trial data. For example, data management device 120 may receive additional information relating to the conditions of a patient after taking an experimental drug as part of the information responsive to the inquiry. Data management device 120 may also update the trial data stored in database 150 and/or database 260 by, for example, updating the relevant information of the patient. By way of example, the trial data may include an electronic health record associated with the patient. Data management device 120 may update the electronic health record to include the additional information received from clinical device 110.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer-readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for creating a query for a trial, the system comprising:
   at least one processor programmed to:
   cause a computing device associated with a sponsor of the trial to display a graphical user interface comprising a plurality of patient identifiers associated with the trial;
   receive, from the computing device, a selection of one of the plurality of patient identifiers;
   receive, from the computing device, a query comprising an inquiry relating to the selected patient identifier;
   determine a practice site associated with the selected patient identifier based on a database storing information associated with a plurality of trials; and
   transmit the query to the practice site associated with the selected patient identifier.

2. The system of claim 1, wherein the at least one processor is further programmed to:
   receive, from the practice site, a response to the query; and
   cause at least a portion of the received response to be displayed by the computing device associated with the sponsor.

3. The system of claim 1, wherein the selected patient identifier is associated with a link configured to enable a user associated with the sponsor to access an electronic health record associated with the patient identifier.

4. The system of claim 1, wherein the graphical user interface further comprises a selectable area for creating the query.

5. A graphical user interface for managing one or more queries associated with a trial, the graphical user interface comprising:
   a query information area displaying information identifying a plurality of queries associated with the trial, wherein the information identifying the plurality of queries comprises at least a query type and a query status of each of the plurality of queries;
   a first search field configured to enable a user to search for a patient identifier associated with one or more of the plurality of queries;
   a second search field configured to enable the user to search for a practice site among a plurality of practice sites, each of the plurality of queries being associated with one or more of the plurality of practice sites in a database; and
   a selectable area configured to enable the user to create a new query.

6. The graphical user interface of claim 5, wherein the information identifying the plurality of queries further comprises at least one of a creation date for each of the plurality of queries, a response date for at least one of the plurality of queries, or a patient identifier for each of the plurality of queries.

7. The graphical user interface of claim 5, wherein the query type for each of the plurality of queries comprises at least one of a trial inclusion criteria type, a trial exclusion criteria type, a consent process type, a patient status type, or tissue sample type; and the query status for each of the plurality of queries comprises at least one of an open status, a closed status, an answered status, or a cancelled status.

8. A system for managing trial data, the system comprising:
   at least one processor programmed to:
   cause a computing device associated with a practice site to display a user interface configured to display a query for a trial conducted at the practice site, wherein the query comprises an inquiry relating to at least one patient included in the trial, the computing device being selected to receive the query based on a database storing information associating the at least one patient with the practice site;
   receive, from the computing device, information responsive to the inquiry included in the query; and
   update, based on the received information, a database storing the trial data.

9. The system of claim 8, wherein the at least one processor is further programmed to transmit the received information to a computing device associated with a sponsor of the trial.

10. The system of claim 9, wherein the at least one processor is further programmed to modify, redact, or remove at least one word included in the received information prior to transmitting the received information to the computing device associated with the sponsor of the trial.

11. The system of claim 8, wherein the query is associated with a patient and the received information is associated with a link providing access to an electronic health record of the patient.

12. A system for managing queries for patient trials, the system comprising:
   at least one processor programmed to:
   receive a first query, wherein the first query comprises an inquiry associated with a first patient enrolled in a first trial;
   receive a second query, wherein the second query comprises an inquiry associated with a second patient enrolled in a second trial;
   determine a first practice site associated with the first patient and a second practice site associated with the second patient based on a database storing information associated with a plurality of trials;
   cause a first computing device associated with the first practice site to display a first graphical user interface comprising the first query;
   cause a second computing device associated with the second practice site to display a second graphical user interface comprising the second query;
   receive, from the first computing device, a response to the first query; and
   receive, from the second computing device, a response to the second query.

13. The system of claim 12, wherein the first query and the second query are received from a third computing device associated with a sponsor of the first and second trials, and wherein the at least one processor is further programmed to:
   cause the third computing device to display a graphical user interface configured to receive the first and second queries.

14. The system, of claim 12, wherein the graphical user interface is further configured to display a list of a plurality of trials associated with the sponsor.

15. The system of claim 14, wherein the at least one processor is further configured to receive, from the third computing device, a selection of one of the plurality of trials associated with the sponsor.

16. The system of claim 15, wherein the at least one processor is further configured to cause the third computing device to display a plurality of patient identifiers associated with selected trial.

17. The system of claim 12, wherein the first query or the second query comprises at least one of a trial identifier, a patient identifier, or a query type.

18. The system of claim 1, wherein the second search field is configured to enable the user to search for the practice site based on at least one of the patient identifier or a trial identifier.

19. The system of claim 10, wherein the at least one word is associated with personally identifiable information.

* * * * *